(12) United States Patent
Chen et al.

(10) Patent No.: US 10,898,143 B2
(45) Date of Patent: Jan. 26, 2021

(54) QUANTITATIVE MAPPING OF CEREBROVASCULAR REACTIVITY USING RESTING-STATE FUNCTIONAL MAGNETIC RESONANCE IMAGING

(71) Applicant: BAYCREST CENTRE, Toronto (CA)

(72) Inventors: Jing Jean Chen, Toronto (CA); Ali M. Golestani, Toronto (CA); Luxi Wei, Toronto (CA)

(*) Notice: Subject to any disclaimer, the term of this patent is extended or adjusted under 35 U.S.C. 154(b) by 415 days.

(21) Appl. No.: 15/348,017

(22) Filed: Nov. 10, 2016

(65) Prior Publication Data

US 2017/0128025 A1 May 11, 2017

Related U.S. Application Data

(60) Provisional application No. 62/253,440, filed on Nov. 10, 2015.

(51) Int. Cl.
| | |
|---|---|
| A61B 5/00 | (2006.01) |
| G01R 33/563 | (2006.01) |
| G01R 33/567 | (2006.01) |
| A61B 5/055 | (2006.01) |
| A61B 5/0205 | (2006.01) |
| A61B 5/026 | (2006.01) |
| A61B 5/091 | (2006.01) |
| A61B 5/087 | (2006.01) |

(52) U.S. Cl.
CPC .......... *A61B 5/7278* (2013.01); *A61B 5/0205* (2013.01); *A61B 5/0263* (2013.01); *A61B 5/055* (2013.01); *A61B 5/7203* (2013.01); *G01R 33/5635* (2013.01); *G01R 33/5673* (2013.01); *A61B 5/087* (2013.01); *A61B 5/091* (2013.01); *A61B 2576/026* (2013.01)

(58) Field of Classification Search
CPC ..... A61B 5/7278; A61B 5/0263; A61B 5/055; A61B 5/0205; A61B 5/7203; A61B 2576/026; A61B 5/091; A61B 5/087; G01R 33/5635; G01R 33/5673; G01R 33/4806; G16H 30/40
See application file for complete search history.

(56) References Cited

U.S. PATENT DOCUMENTS

2009/0120435 A1* 5/2009 Slessarev .......... A61M 16/0051
128/203.14

OTHER PUBLICATIONS

Birn, et al., in "Separating respiratory-variation-related fluctuations from neuronal-activity-related fluctuations in fMRI," NeuroImage, 2006; 31:1536-1548.
Chang, C., et al., in "Influence of heart rate on the BOLD signal: the cardiac response function," NeuroImage, 2009; 44:857-869.
Glover, et al., in "Image-based method for retrospective correction of physiological motion effects in fMRI: RETROICOR," Magn Reson Med, 2000; 44:162-167.

(Continued)

*Primary Examiner* — Hien N Nguyen
(74) *Attorney, Agent, or Firm* — Quarles & Brady LLP

(57) ABSTRACT

Described here are systems and methods for estimating a quantitative measure of cerebrovascular reactivity ("CVR") from data acquired using resting-state functional magnetic resonance imaging ("fMRI").

14 Claims, 12 Drawing Sheets

(56) References Cited

OTHER PUBLICATIONS

Golestani, A.M. et al., in "Mapping the end-tidal CO2 response function in the resting-state Bold fMRI signal: Spatial specificity, test-retest reliability and effect of fMRI sampling rate," NeuroImage, 2015; 104:266-277.
Kannurpatti S.S. et al, "Detection and scaling of task-induced fMRI-BOLD response using resting state fluctuations," NeuroImage, 2008; 40:1567-1574.
Lindquist et al., "Modeling the hemodynamic response function in fMRI: efficiency, bias and mis-modeling," NeuroImage, 2009; 45:187-98.
Setsompop, et al., in "Blipped-controlled aliasing in parallel imaging for simultaneous multislice echo planer imaging with reduced g-factor penalty," Magn Reson Med, 2011; doi: 10.1002/mrm.23097.
Slessarev, et al., in "Prospective targeting and control of end-tidal CO2 and O2 concentrations," J Physiol, 2007; 581:1207-1219.
Wise, R.G. et al., in "Resting fluctuations in arterial carbon dioxide induce significant low frequency variations in BOLD signal," NeuroImage, 2004; 21:1652-1664.
Tang, Y.F, et al., in "Altered baseline brain activity in children with ADHD revealed by resting-state functional MRI," Brain and Development, 2007; 29:83-91.

* cited by examiner

QUANTITATIVE MAPPING OF CEREBROVASCULAR REACTIVITY USING RESTING-STATE FUNCTIONAL MAGNETIC RESONANCE IMAGING

CROSS-REFERENCE TO RELATED APPLICATIONS

This application claims the benefit of U.S. Provisional Patent Application Ser. No. 62/253,440, filed on Nov. 10, 2015, and entitled "QUANTITATIVE MAPPING OF CEREBROVASCULAR REACTIVITY USING RESTING-STATE FUNCTIONAL MAGNETIC RESONANCE IMAGING."

BACKGROUND OF THE DISCLOSURE

Cerebrovascular reactivity ("CVR") is an important metric of cerebrovascular health, and which refers to the degree of vasodilatation or constriction in response to a vascular agent or respiratory task. CVR is an indication of vascular reserve and autoregulatory efficiency, and its impairment is often identified with cerebrovascular diseases.

Clinically, CVR measurements benefit the treatment of cerebrovascular diseases through better assessment of disease severity and prediction of treatment outcome. For instance, impaired CVR has been associated with risk for stroke and transient ischemic attacks. Given similar diagnoses, individuals with CVR impairment have a much higher risk of disabling stroke than those without. In addition, reduced CVR has also been cited as a marker for lacunar infarction, microbleeding, as well as cortical atrophy and cognitive decline in individuals at risk of stroke. Furthermore, CVR is of direct diagnostic value in our management of patients with cerebrovascular diseases. Embolic occlusions are associated with normal CVR and can be medicinally treated, but a stenosis, associated with CVR abnormalities, is often surgically treated. However, conventional forms of CVR measurement are often inappropriate for those with severe disease risk.

CVR is commonly mapped using the functional magnetic resonance imaging ("fMRI") response to vasodilating agents. Vascular agents used for CVR measurement generally include acetazolamide injection and respiratory manipulations. While acetazolamide injections are invasive and have been associated with adverse and potentially long-lasting side effects, respiratory manipulations are relatively non-invasive and safe. These manipulations induce changes in the subject's end-tidal CO2 pressure (PETCO2), a surrogate for intravascular CO2.

CO2 is a potent vasodilator, triggering changes in vascular tone through the arterial baroflex. PETCO2 elevation (hypercapnia) can be induced through manually adjusted administration of blended gases, end-tidal forcing, or more recently, computerized PETCO2 targeting. The latter method provides immediate and robust PETCO2 changes. More recently, breath-holding and hypocapnia have been proposed as alternatives to modulate PETCO2, although hypercapnia is still the dominating approach.

The vascular response to CO2 is well established. Typically, CVR is measured as the ratio between BOLD signal change and PETCO2 change (by virtue of CBF-BOLD coupling). Generally, respiration-challenge based conventional quantitative CVR measurement (qCVR) approaches require lengthy subject preparations and strict subject cooperation, and are particularly challenging in patients. In addition, the various styles of breath-holding can introduce difficulties in comparing CVR values across populations. Moreover, in hypercapnia, undesirable perturbations in neuronal activity due to the sometimes large PETCO2 changes can compromise the accuracy of conventional CVR measures.

More concerning are unwanted side effects of conventional CVR tasks, which may be harmful in certain patient types. Often, patients do not fulfill the inclusion criteria for the existing CVR measurement approach. Based on prior literature, amongst cerebrovascular disease patients, up to 24.3% are unable to complete the study. Amongst older adults, up to 30% are unable to complete respiratory tasks such as breath-holding. These considerations significantly limit the applicability of conventional CVR techniques to patients, and are particularly prohibitive to those at risk of disease. However, the requirement of using external agents makes CVR measurement challenging in many clinical situations, often being intolerable to the very populations at risk of cerebrovascular disease.

Thus, there remains a need to provide a method for the measurements of CVR that is based solely on resting-state fMRI, without the need for invasive agents or respiratory manipulations.

SUMMARY OF THE DISCLOSURE

The present disclosure overcomes the aforementioned drawbacks by providing a method for estimating a quantitative cerebrovascular reactivity measure from resting-state functional magnetic resonance imaging data. The method includes providing resting-state functional magnetic resonance imaging (rs-fMRI) data acquired from a subject with a magnetic resonance imaging (MRI) system, the rs-fMRI data comprising blood-oxygen level dependent (BOLD) signals, and providing physiological data acquired from the subject while the rs-fMRI data were acquired, the physiological data comprising cardiac-rate variability (CRV) signals, respiratory-volume variability (RVT) signals, and passive end-tidal carbon dioxide (PETCO2) signals. The BOLD signals are processed to remove BOLD signal variations attributable to the CRV and RVT signals, and a quantitative cerebrovascular reactivity (qCVR) measure is estimated from the processed BOLD signals by further processing the BOLD signals to remove BOLD signal variations attributable to the PETCO2 signals.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is made therefore to the claims and herein for interpreting the scope of the invention.

BRIEF DESCRIPTION OF THE DRAWINGS

FIG. 9A shows an average across all 16 subjects in an example study, and FIG. 9B shows maps for a sample subject.

In FIG. 14A, the shapes of the whole-brain average $HRF_{CO2}$ estimates are similar (group average, N=8). The amplitude (FIG. 14B) and time of onset (TTP) (FIG. 14C) of the estimates were also found to be reproducible in various brain regions, using both conventional and accelerated imaging, as quantified through the cosine similarity index (reproducibility threshold=0.9, outlined in green).

DETAILED DESCRIPTION OF THE INVENTION

Described here are systems and methods for estimating a quantitative measure of cerebrovascular reactivity ("CVR") from data acquired using resting-state functional magnetic resonance imaging ("fMRI").

The increasing prevalence of cerebrovascular diseases represents a serious burden for healthcare, and highlights of the importance of regularly monitoring cerebrovascular health in those at risk of disease. One of the most valuable indicators of cerebrovascular health is CVR, but CVR is conventionally only obtainable using invasive vasoactive agents or respiratory challenges, making clinical implementation challenging. In response, the systems and methods of the present disclosure provide a technique to assess CVR based solely on resting-state fMRI data. Exploiting the effect of intrinsic respiratory variability on the rs-fMRI signal, the systems and methods of the present disclosure eliminate the need for vascular agents or task challenges. Thus, the systems and methods of the present disclosure can be applied even to those subjects who have lost consciousness due to illnesses or sedation. It is contemplated that the systems and methods described here will open up numerous new opportunities to use resting-state fMRI, facilitating the extension of the versatile technique into routine clinical use.

Figure 1:
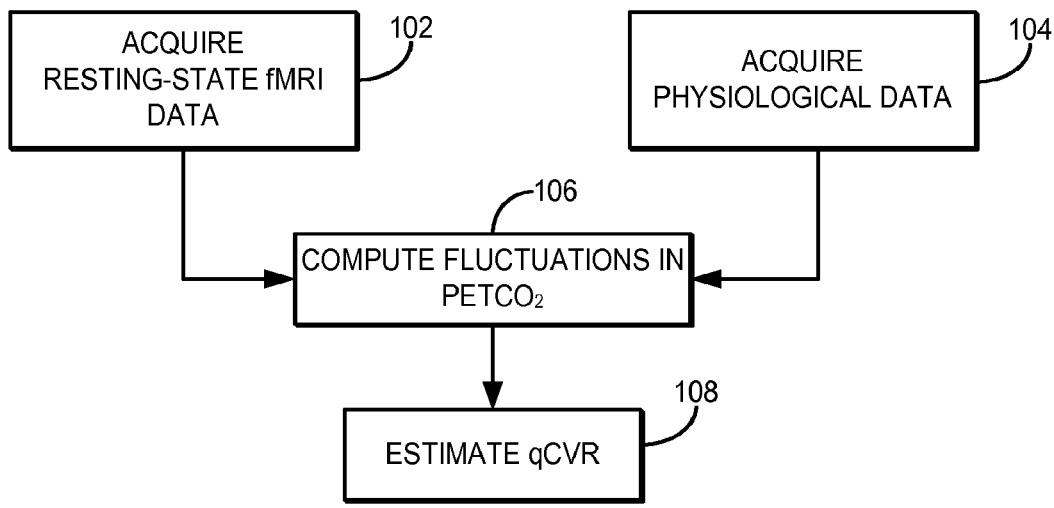
FIG. 1 is a flowchart setting forth the steps of an example method for computing a quantitative measure of CVR ("qCVR") from data acquired using resting-state fMRI ("rs-fMRI").

Referring now to FIG. 1, a flowchart is illustrated as setting forth the steps of an example method for computing a quantitative measure of CVR ("qCVR") from data acquired using resting-state fMRI ("rs-fMRI"). The method includes acquiring resting-state fMRI data from a subject, as indicated at step 102. While the rs-fMRI data are acquired, physiological data are also acquired from the subject, as indicated at step 104.

The acquired physiological data preferably includes the subject's heart rate, respiration pattern, and end-tidal $CO_2$ pressure ("$PETCO_2$"). For instance, acquiring the subject's heart rate can be implemented using a finger pulse oximeter, and the subject's respiration pattern can be acquired using a pressure-sensitive respiration belt. Recordings from the pressure-sensitive belt are linearly proportional to lung expansion, and thus reflect respiration. $PETCO_2$ measurements can be passively monitored using a breathing circuit connected to a gas controller, such as the RespirAct™ system (Thornhill Research; Toronto, Canada). Other alternatives for obtaining $PETCO_2$ measurements include using a Biopac™ system (Biopac Systems, Inc.; California), or a capnometer with a quantitative $CO_2$ sensor.

Based on the acquired physiological data, fluctuations in $PETCO_2$ are computed, as indicated at step 106. As an example, the fluctuations in $PETCO_2$ can comprise a trace or other data that indicate the fluctuations in $PETCO_2$ as a function of time. Using the acquired rs-fMRI data and the fluctuations in $PETCO_2$, a qCVR measure is estimated, as indicated at step 108. In general the qCVR measure can be estimated based, in part, on isolating and removing the effects of the intrinsic end-tidal $CO_2$ variability on the rs-fMRI signals, and described in more detail below.

Figure 2:
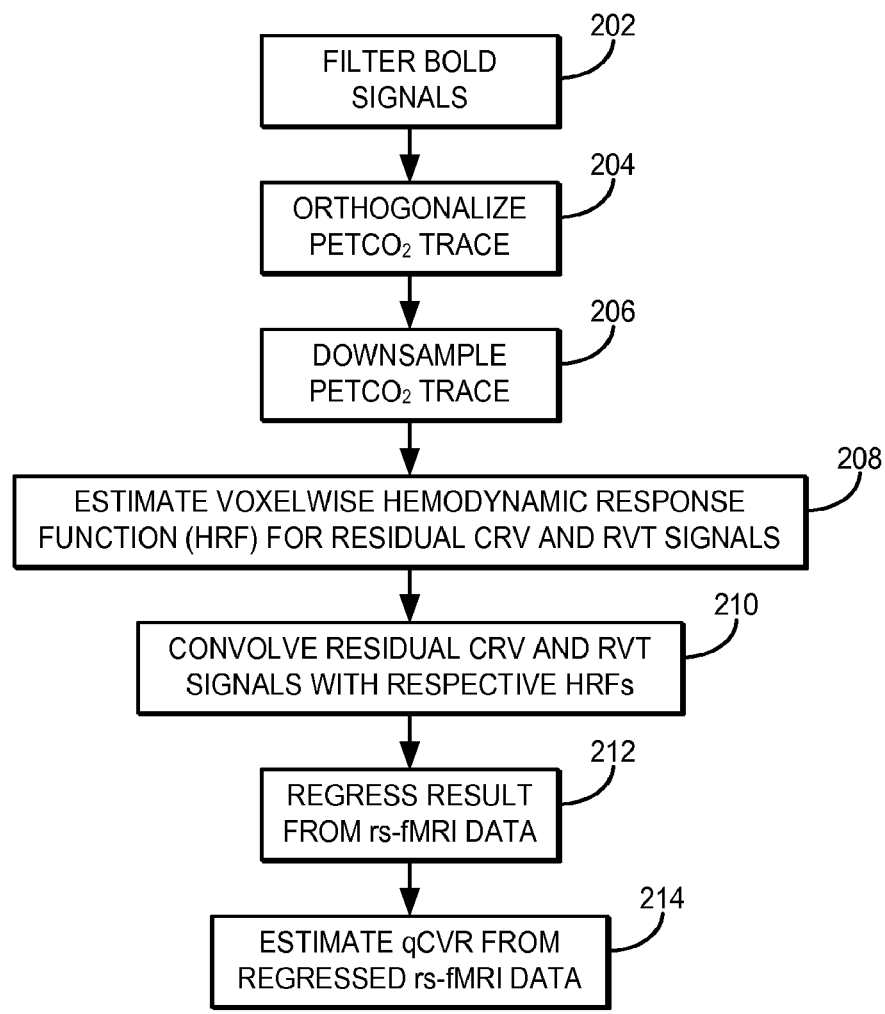
FIG. 2 is a flowchart setting forth the steps of an example method for estimating a qCVR measure based on rs-fMRI data, cardiac-rate variability, respiratory-volume variability, and $PETCO_2$ fluctuation data.

Referring now to FIG. 2, a flowchart is illustrated as setting forth the steps of an example method for estimating a qCVR measure based on rs-fMRI data, cardiac-rate variability, respiratory-volume variability, and $PETCO_2$ fluctuation data. The method includes filtering the blood-oxygen level dependent ("BOLD") signals contained in the rs-fMRI data, as indicated at step 202. As one example, the BOLD signals can be bandpass filtered to remove information outside of the relevant spectral range. For instance, the BOLD signals can be bandpass filtered using a bandpass ranging from 0.005 Hz and 0.4 Hz. In some instances, the first few frames of the rs-fMRI data can be discarded prior to filtering. As an example, the first 20 time frames can be discarded.

A trace of the $PETCO_2$ fluctuations is then orthogonalized, as indicated at step 204. For instance, the $PETCO_2$ trace can be orthogonalized against cardiac-rate variability ("CRV") and respiratory-volume variability ("RVT") signals acquired as physiological data during the acquisition of the rs-fMRI data. As one example, the $PETCO_2$ trace can be orthogonalized using a Gram-Schmidt process or similar technique for orthogonalizing vectors. As a result, the CRV, RVT, and $PETCO_2$ signals can be represented by a common orthogonal basis.

The orthogonalized $PETCO_2$ trace is then downsampled to the same sampling rate as the BOLD signals, as indicated at step 206. Voxelwise hemodynamic response functions ("HRFs") for residual CRV and RVT signals are then estimated, as indicated at step 208. As one example, these HRFs can be estimated based on a multi-variate deconvolution model. An example of such a multi-variate deconvolution model is described by A. M. Golestani, et al., in "Mapping the end-tidal $CO_2$ response function in the resting-state BOLD fMRI signal: Spatial specificity, test-retest reliability and effect of fMRI sampling rate," *NeuroImage*, 2015; 104:266-277. The residual CRT and RVT signals are then convolved with the respective HRFs on a voxel-by-voxel basis, as indicated at step 210. The results of the convolution performed in step 210 are then regressed from the pre-processed BOLD signals, as indicated at step 212.

The qCVR measure is then estimated from the processed BOLD signals, as indicated at step 214. In general, the qCVR measure is estimated from the relationship between the resting-state BOLD signals and the $PETCO_2$ fluctuations. In some embodiments, this relationship is determined based on a cross-correlation technique, described below. In some other embodiments, the relationship is determined based on a parametric deconvolution technique, also described below.

Figure 3:
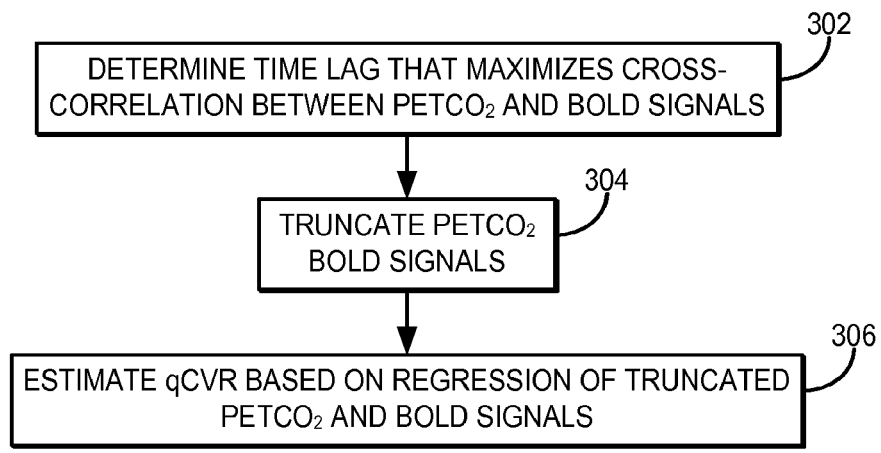
FIG. 3 is a flowchart setting forth the steps of an example method for estimating qCVR using a cross-correlation technique.

Referring now to FIG. 3, a flowchart is illustrated as setting forth the steps of an example method for estimating qCVR using a cross-correlation technique. In general, the cross-correlation technique is based on the assumption that increases in $PETCO_2$ will result in an increase in the resting-state BOLD signal.

The method includes cross-correlating the $PETCO_2$ signals and the BOLD signals to find a time lag that maximizes the cross correlation, as indicated at step 302. The BOLD signal is shifted one frame at a time, and is assumed to always lag the $PETCO_2$ signal. Voxels with lag greater than a threshold amount (e.g., 100 frames) do not conform with physiological restrictions and thus can be ignored.

Subsequently, both the BOLD and $PETCO_2$ signals are truncated to contain only the overlapping, maximally cross-correlated, segment as indicated at step 304. At this point, any frames that are more than two standard deviations away from the mean of either one of the signals can optionally be discarded as outliers.

Figures 4A, 4B:
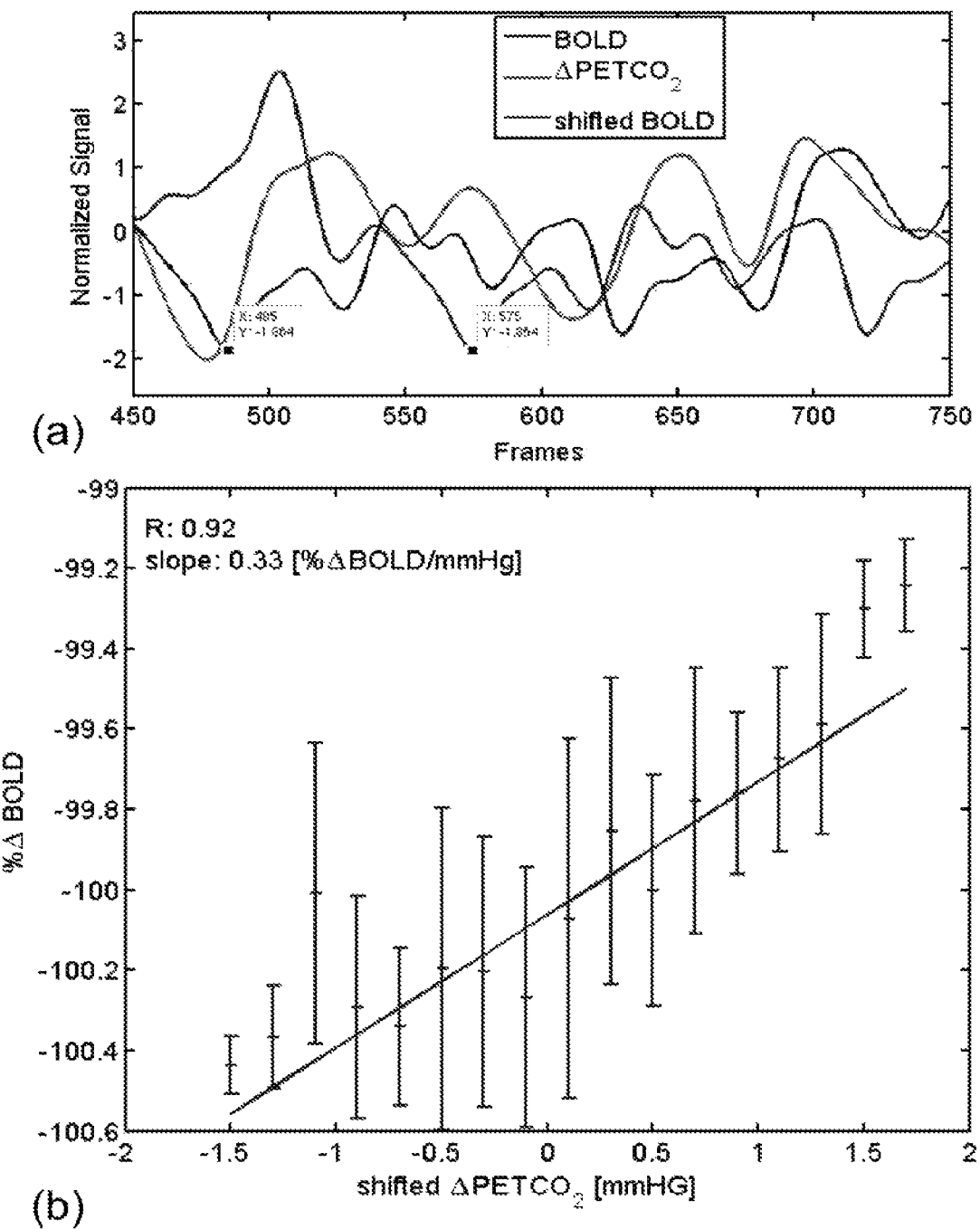
FIGS. 4A-4B depict sections of the time traces for the BOLD signal at a single voxel, ΔPETCO2, and the optimally shifted ΔPETCO2 measurements (FIG. 4A). A sample linear fit of a single-voxel BOLD time series to the shifted ΔPETCO2 time course is shown in FIG. 4B, with the slope of the fit designated as the qCVR measure.

Finally, the $PETCO_2$ signal was regressed against the BOLD signal using a least squares method, and the slope of this fit was recorded for each voxel as the CVR estimate, as indicated at step 306. An example of such a linear regression is illustrated in FIGS. 4A and 4B, with the slope in units of % ΔBOLD/mmHg, and which are described below in more detail.

Physiologically speaking, CVR values should be positive. However, the combination of low vascular structure, response, and signal to noise ratio in the white matter could result in negative CVR values in some voxels. Therefore, as a last step, all negative CVR values can optionally be clamped to zero.

In the work by R. G. Wise, et al., in "Resting fluctuations in arterial carbon dioxide induce significant low frequency variations in BOLD signal," *NeuroImage*, 2004; 21:1652-1664, a canonical HRF that was estimated using transcranial Doppler flowmetry, was applied when estimating the fractional BOLD effect due to $PETCO_2$. Voxel-wise deconvolution within a multiregression model can be used to estimate the HRF for $PETCO_2$ ($HRF_{CO2}$). However, as the deconvolution process is highly sensitive to noise, the immediate results of the deconvolution may not always yield physiologically plausible HRF shapes. That is, the voxel-wise HRFs may contain non-physiological oscillations, which is particularly problematic for a voxel-wise CVR estimation that is dependent on the HRF amplitude. To overcome this challenge, a parametric deconvolution approach is implemented.

Figure 5:
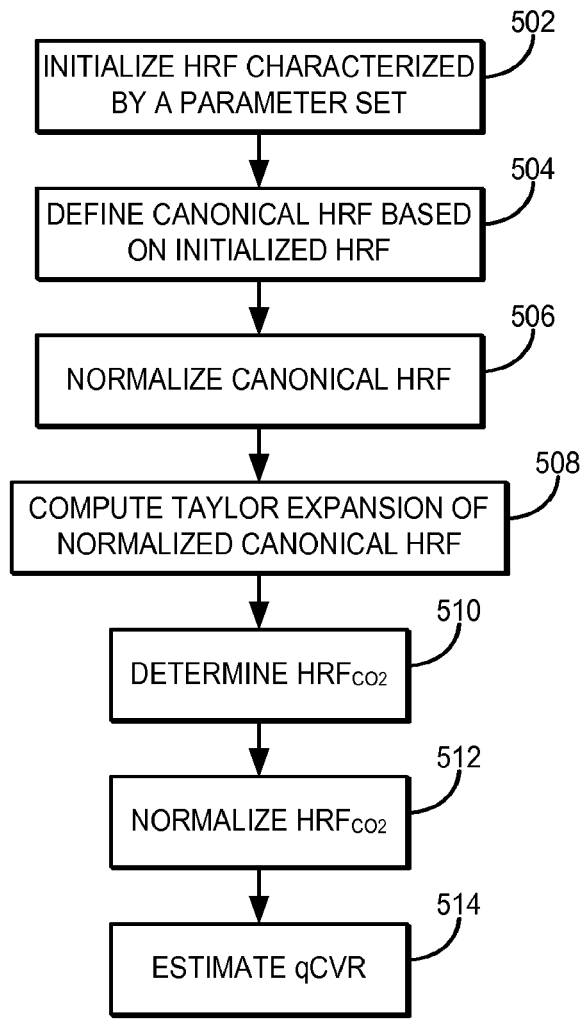
FIG. 5 is a flowchart setting forth the steps of an example method for estimating qCVR using a parametric deconvolution technique.

Referring now to FIG. 5, a flowchart is illustrated as setting forth the steps of an example method for estimating qCVR using a parametric deconvolution technique. In general, this technique includes fitting $PETCO_2$ time courses to the BOLD signals with the goal of parameterizing a $HRF_{CO2}$ constructed from variants of a canonical HRF. Thus, the method includes initializing an HRF estimate characterized by a parameter set, p, as indicated at step 502. The parameter set can include the following, $$p=[p(1)\ p(2)\ p(3)\ p(4)\ p(5)\ p(6)\ p(7)] \quad (1);$$

where the parameters are defined as p(1) being the delay of response relative to onset, which as one example can be set to 6 seconds; p(2) being the delay of undershoot relative to onset, which as one example can be set to 16 seconds; p(3) being the dispersion of response, which as one example can be set to 1 second; p(4) being the dispersion of undershoot, which as one example can be set to 1 second; p(5) being the ratio of response to undershoot, which as one example can be set to 6 seconds; p(6) being the response onset, which as one example can be set to zero seconds; and p(7) being the length of kernel, which as one example can be set to 32 seconds. Thus, as one example, the parameter set can be defined as the following, with each entry having units of seconds:

$$p=[6\ 16\ 1\ 1\ 6\ 0\ 32] \quad (2).$$

As another example, the following parameter set (entries in seconds) was empirically determined to fit well to resting fluctuations in $PETCO_2$:

$$p=[15\ 25\ 1\ 1\ 4\ 0\ 40] \quad (3).$$

The parameters p(6) and p(7) are used to define a time vector (or kernel), t, that can be used to generate the canonical HRF, which is defined as, $$HRF_{CO_2} = [A\ B\ C] \cdot \begin{bmatrix} basis_1 \\ basis_2 \\ basis_3 \end{bmatrix}. \quad (5)$$

where Γ(·) is the gamma function, $\alpha_1=p(1)/p(3)$, $\alpha_2=p(2)/p(4)$, $\beta_1=1/p(3)$, $\beta_2=1/p(4)$, $c=1/p(5)$, and A specifies the HRF amplitude. Thus, the canonical HRF can be defined based on the initialized HRF, as indicated at step 504. Before fitting the data to the HRF-based model, the canonical HRF is normalized such that its area is equal to unity, as indicated at step 506.

From the canonical HRF, the Taylor expansion in time (temporal derivative) and width (dispersion derivative) is calculated, as indicated at step 508 and presented in Lindquist et al., "Modeling the hemodynamic response function in fMRI: efficiency, bias and mis-modeling," *NeuroImage*, 2009; 45:187-98. The $HRF_{CO2}$ is then determined based on the canonical HRF and its Taylor expansion, as indicated at step 510. For instance, the canonical HRF, its temporal derivative, and its dispersion derivative can be designated as basis functions $basis_1$, $basis_2$ and $basis_3$, respectively, thereby forming a basis set to account for varying response delay and spread of response at each voxel, $$HRF_{canonical}(t) = A\left(\frac{t^{\alpha_1-1}\beta_1^{\alpha_1}e^{-\beta_1 t}}{\Gamma(\alpha_1)} - c \cdot \frac{t^{\alpha_2-1}\beta_2^{\alpha_2}e^{-\beta_2 t}}{\Gamma(\alpha_2)}\right); \quad (4)$$

The parameters A, B, and C in Eqn. (5) characterize the relative contribution of each basis function at each voxel, and are determined through least-squares minimization of the difference between the measured BOLD signal and the convolution between $HRF_{CO_2}$ and the $PETCO_2$ time course.

Figures 6A, 6B:
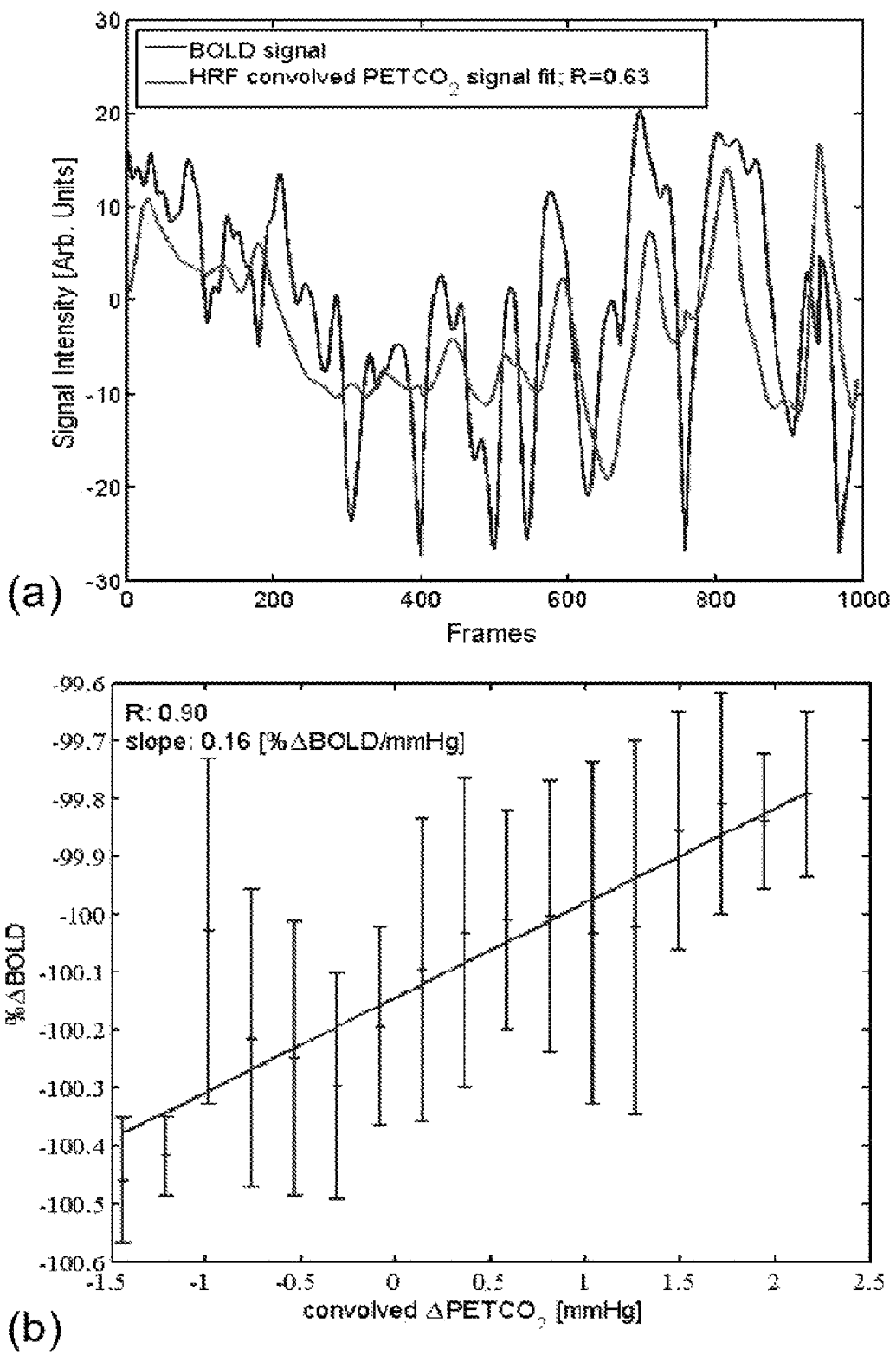
FIGS. 6A-6B depict a single-voxel BOLD time course overlaid by the fitted time course resulting form the convolution of ΔPETCO2 and $HRF_{CO2}$ (FIG. 6A). The corresponding linear fit is shown FIG. 6B, and qCVR is determined as the slope of the fit.

Next, the $HRF_{CO_2}$ is normalized such that its sum is equal to unity, as indicated at step 512. Finally, the qCVR measure can be estimated based on a convolution of the $PETCO_2$ time course with the normalized voxel-wise $HRF_{CO_2}$. For instance, the result of this convolution can be regressed against the preprocessed BOLD signal at each voxel, and the slope of this regression taken as the resting state CVR (rsCVR), with the unit of %ΔBOLD/mmHg. A sample regression fit is shown in FIGS. 6A and 6B, which are described below in more detail.

Figure 7:
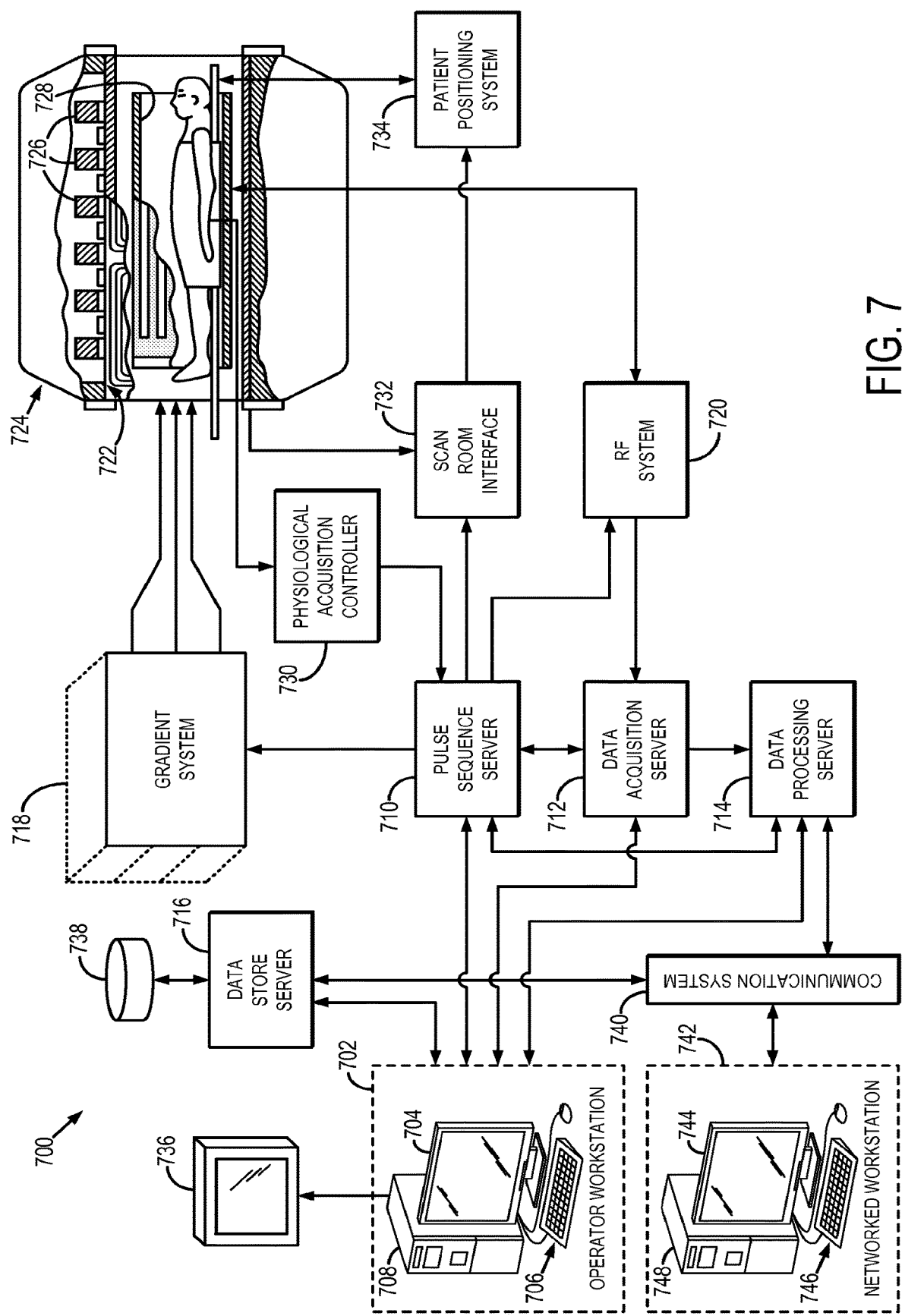
FIG. 7 is a block diagram of an example of a magnetic resonance imaging ("MRI") system.

Referring particularly now to FIG. 7, an example of a magnetic resonance imaging ("MRI") system 700 that can implement the methods described above is illustrated. The MRI system 700 includes an operator workstation 702, which will typically include a display 704; one or more input devices 706, such as a keyboard and mouse; and a processor 708. The processor 708 may include a commercially available programmable machine running a commercially available operating system. The operator workstation 702 provides the operator interface that enables scan prescriptions to be entered into the MRI system 700. In general, the operator workstation 702 may be coupled to four servers: a pulse sequence server 710; a data acquisition server 712; a data processing server 714; and a data store server 716. The operator workstation 702 and each server 710, 712, 714, and 716 are connected to communicate with each other. For example, the servers 710, 712, 714, and 716 may be connected via a communication system 740, which may include any suitable network connection, whether wired, wireless, or a combination of both. As an example, the communication system 740 may include both proprietary or dedicated networks, as well as open networks, such as the Internet.

The pulse sequence server 710 functions in response to instructions downloaded from the operator workstation 702 to operate a gradient system 718 and a radiofrequency ("RF") system 720. Gradient waveforms necessary to perform the prescribed scan are produced and applied to the gradient system 718, which excites gradient coils in an assembly 722 to produce the magnetic field gradients $G_x$, $G_y$, and $G_z$ used for position encoding magnetic resonance signals. The gradient coil assembly 722 forms part of a magnet assembly 724 that includes a polarizing magnet 726 and a whole-body RF coil 728.

RF waveforms are applied by the RF system 720 to the RF coil 728, or a separate local coil (not shown in FIG. 7), in order to perform the prescribed magnetic resonance pulse sequence. Responsive magnetic resonance signals detected by the RF coil 728, or a separate local coil (not shown in FIG. 7), are received by the RF system 720, where they are amplified, demodulated, filtered, and digitized under direction of commands produced by the pulse sequence server 710. The RF system 720 includes an RF transmitter for producing a wide variety of RF pulses used in MRI pulse sequences. The RF transmitter is responsive to the scan prescription and direction from the pulse sequence server 710 to produce RF pulses of the desired frequency, phase, and pulse amplitude waveform. The generated RF pulses may be applied to the whole-body RF coil 728 or to one or more local coils or coil arrays (not shown in FIG. 7).

The RF system 720 also includes one or more RF receiver channels. Each RF receiver channel includes an RF preamplifier that amplifies the magnetic resonance signal received by the coil 728 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \quad (6);$$

and the phase of the received magnetic resonance signal may also be determined according to the following relationship:

$$\varphi = \tan^{-1}\left(\frac{Q}{I}\right). \quad (7)$$

The pulse sequence server 710 also optionally receives patient data from a physiological acquisition controller 730. By way of example, the physiological acquisition controller 730 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 710 to synchronize, or "gate," the performance of the scan with the subject's heart beat or respiration.

The pulse sequence server 710 also connects to a scan room interface circuit 732 that receives signals from various sensors associated with the condition of the patient and the magnet system. It is also through the scan room interface circuit 732 that a patient positioning system 734 receives commands to move the patient to desired positions during the scan.

The digitized magnetic resonance signal samples produced by the RF system 720 are received by the data acquisition server 712. The data acquisition server 712 operates in response to instructions downloaded from the operator workstation 702 to receive the real-time magnetic resonance data and provide buffer storage, such that no data is lost by data overrun. In some scans, the data acquisition server 712 does little more than pass the acquired magnetic resonance data to the data processor server 714. However, in scans that require information derived from acquired magnetic resonance data to control the further performance of the scan, the data acquisition server 712 is programmed to produce such information and convey it to the pulse sequence server 710. For example, during prescans, magnetic resonance data is acquired and used to calibrate the pulse sequence performed by the pulse sequence server 710. As another example, navigator signals may be acquired and used to adjust the operating parameters of the RF system 720 or the gradient system 718, or to control the view order in which k-space is sampled. In still another example, the data acquisition server 712 may also be employed to process magnetic resonance signals used to detect the arrival of a contrast agent in a magnetic resonance angiography ("MRA") scan. By way of example, the data acquisition server 712 acquires magnetic resonance data and processes it in real-time to produce information that is used to control the scan.

The data processing server 714 receives magnetic resonance data from the data acquisition server 712 and processes it in accordance with instructions downloaded from the operator workstation 702. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 714 are conveyed back to the operator workstation 702 where they are stored. Real-time images are stored in a data base memory cache (not shown in FIG. 7), from which they may be output to operator display 702 or a display 736 that is located near the magnet assembly 724 for use by attending physicians. Batch mode images or selected real time images are stored in a host database on disc storage 738. When such images have been reconstructed and transferred to storage, the data processing server 714 notifies the data store server 716 on the operator workstation 702. The operator workstation 702 may be used by an operator to archive the images, produce films, or send the images via a network to other facilities.

The MRI system 700 may also include one or more networked workstations 742. By way of example, a networked workstation 742 may include a display 744; one or more input devices 746, such as a keyboard and mouse; and a processor 748. The networked workstation 742 may be located within the same facility as the operator workstation 702, or in a different facility, such as a different healthcare institution or clinic.

The networked workstation 742, whether within the same facility or in a different facility as the operator workstation 702, may gain remote access to the data processing server 714 or data store server 716 via the communication system 740. Accordingly, multiple networked workstations 742 may have access to the data processing server 714 and the data store server 716. In this manner, magnetic resonance data, reconstructed images, or other data may be exchanged between the data processing server 714 or the data store server 716 and the networked workstations 742, such that the data or images may be remotely processed by a networked workstation 742. This data may be exchanged in any suitable format, such as in accordance with the transmission control protocol ("TCP"), the internet protocol ("IP"), or other known or suitable protocols.

Example: Quantitative Mapping of Cerebrovascular Reactivity Using Resting-State BOLD fMRI: A Validation in Healthy Adults In an example study, the rs-fMRI signal component associated with $PETCO_2$ variability was estimated as a means to estimate qCVR, and the resulting resting-state qCVR measurements were compared to those obtained using the "gold standard" method.

Methods

Participants.

All experiments were performed on 16 healthy young adults (age=26.5±6.5 years). Screening questionnaires were used to ensure that participants did not suffer from diseases or take medications that might compromise brain function or hemodynamics. All participants were recruited from the Rotman Research Institute Research Participants Database, and were asked to refrain from strenuous exercise for 24 hours and to avoid caffeine/alcohol consumption for 4 hours prior to the scans. Written informed consent was obtained from all participants.

Physiological Monitoring.

The experimental setup used in this study is that described above with respect to FIGS. 1-3 and FIG. 5. During the resting-state functional imaging sessions, heart rate was recorded using the MRI scanner's built-in finger oximeter, attached to the left index finger. This provided estimates of cardiac variability. The subject's respiration pattern was also recorded using a pressure-sensitive respiration belt, connected to the Biopac™ (Biopac Systems, Inc.; California). The belt was attached just below the ribcage. The belt recordings are linearly proportional to lung expansion, and reflect respiration. $PETCO_2$ measurements were passively monitored using a breathing circuit connected to a RespirAct™ system (Thornhill Research; Toronto).

Imaging Protocol.

MRI scans were performed using a 3 Tesla MRI using a 32-channel matrix head coil. Participants were immobilized using head constraints (including a vacuum bag under the chin to control pitch motion). Participants were also be encouraged to voluntarily and freely vary their breathing rate/depth during the scan. The following scans were acquired.

First, a 3D anatomical scan was acquired using an MPRAGE pulse sequence with 1 $mm^3$ isotropic resolution and a GRAPPA acceleration factor of 2. Resting-state BOLD fMRI data were acquired using accelerated scanning. Because it was preferable to accelerate the image acquisition to achieve the most accurate noise removal, a simultaneous multi-slice GE-EPI BOLD technique, such as the one described by K. Setsompop, et al., in "Blipped-controlled aliasing in parallel imaging for simultaneous multislice echo planer imaging with reduced g-factor penalty," *Magn Reson Med*, 2011; doi: 10.1002/mrm.23097, was used. For this scan, the following parameters were used: TR/TE=380/30 ms, flip angle=40°, 20 5-mm slices, 64×64 matrix, 4×4×5 mm voxels. Both magnitude and phase data were acquired in the axial oblique orientation with a total of 1900 measurements (total scan time of 12 min).

A conventional BOLD cerebrovascular reactivity scan was also performed for cross-validation of the proposed method. BOLD-based cerebrovascular reactivity was estimated using the second echo of a dual-echo pseudo-continuous ASL ("pCASL") sequence. In this scan, the following parameters were used: TR=3500 ms, TEBOLD=25 ms, flip angle=90°, 20 slices, 3.44×3.44×6 $mm^3$, 120 volumes. $PETCO_2$ was sinusoidally modulated during the dual-echo pCASL scans with a period of 120 seconds. Three periods of sinusoidal $PETCO_2$ variations were induced with a baseline-to-peak amplitude of ±4 mmHg, following a 1-minute baseline.

All $CO_2$ manipulations were achieved by administering mixtures of $O_2$, $CO_2$ and medical air delivered using the RespirAct™ breathing circuit (Thornhill Research, Toronto, Canada), designed to provide computerized and independent targeting of end-tidal $O_2$ ($PETO_2$) and $CO_2$ ($PETCO_2$) pressure using a sequential gas delivery method, such as the one described by M. Slessarev, et al., in "Prospective targeting and control of end-tidal $CO_2$ and $O_2$ concentrations," *J Physiol*, 2007; 581:1207-1219. This method was chosen to maximize steady-state $PETCO_2$-targetting accuracy and stability while minimizing $PETO_2$ confounds during $CO_2$-based cerebrovascular reactivity measurements.

BOLD Data Preprocessing.

Preprocessing of the rs-fMRI magnitude data included the following steps: (1) retrospective motion correction; (2) slice-timing correction; (3) detrending up to the third order polynomial; and (4) spatial smoothing using a Gaussian kernel. These was performed using AFNI (National Institutes of Health, Bethesda, Md.) and the FEAT package in FSL (FMRIB, Oxford University). Cardiac and respiratory cycles were then regressed out using the RETROICOR method described by G. H. Glover, et al., in "Image-based method for retrospective correction of physiological motion effects in fMRI: RETROICOR," *Magn Reson Med*, 2000; 44:162-167. Running this first-level physiological denoising permitted the minimization of the contribution from irrelevant time-locked signal components, and focusing on the signal components integral to the BOLD response to $CO_2$. Furthermore, slices with excessive motion were discarded. Lastly, the BOLD signal was normalized by its temporal mean to arrive at a % BOLD fluctuation time course.

Physiological Modeling in rs-fMRI.

It is contemplated that the physiological modulation of the rs-fMRI signal can be mainly attributed to fluctuations in $CO_2$, respiratory volume, and heart rate. An aim of this study was to isolate the effects of the intrinsic end-tidal $CO_2$ variability on the rs-fMRI signal, leading to a potential tool for measuring cerebrovascular reactivity. $PETCO_2$ fluctuates over the natural breathing and cardiac cycle. The interactions of $PETCO_2$ with respiratory volume and cardiac-pulsation rate have not been fully accounted for in previous techniques, and thus the unique modulatory effect of $PETCO_2$ on the rs-fMRI signal remained undefined. In order to lay the foundation for the isolation and use of $PETCO_2$ for cerebrovascular reactivity measurements, the relationship between $PETCO_2$ and its concurrent physiological signals (cardiac-rate variability and respiratory-volume variability) was estimated.

Cardiac-rate variability ("CRV") is the variability in heart rate, and has previously been found to strongly modulate the rs-fMRI signal, not only near the cerebrospinal fluid and major blood vessels, but throughout the grey matter. Respiration and cardiac pulsation are related through respiratory sinus arrhythmia, a naturally occurring variation in heart rate during a breathing cycle driven by the parasympathetic nervous system. Breathing rate scales with heart rate as well as heart-rate variability.

Respiratory-volume variability ("RVT") corresponds to changes in breathing pattern, which impact the rs-fMRI signal. Believed to be initiated by random dynamics in the autonomic nervous system, RVT is a slow (~0.03 Hz) breath-to-breath volume variation that is correlated with the BOLD signal in a pattern similar to that of $PETCO_2$, and to BOLD maps associated with breath-holding, which suggests a partially similar, but not identical, mechanism.

Figure 8:
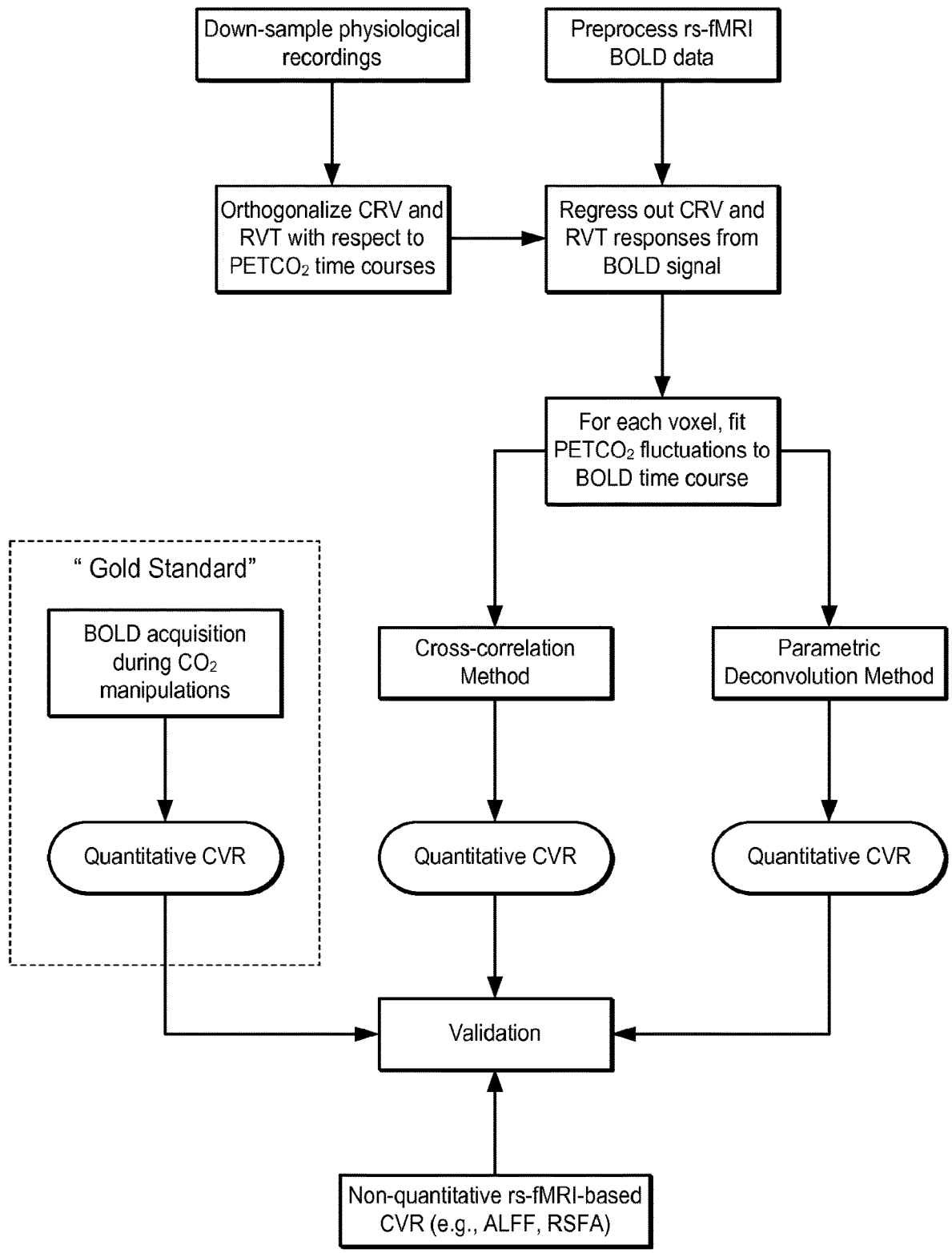
FIG. 8 is a schematic representation of a methodology and validation approach. Validation of the rs-fMRI-based quantitative CVR estimates are the focus of this work.

The schematic for the qCVR estimation and validation strategy is shown in FIG. 8. As mentioned previously, intravascular $CO_2$ variations (through $PETCO_2$) are focused on while accounting for effects of respiratory-volume variability and cardiac-rate variability, which are intrinsically related to respiration. RVT and CRV were computed as described, respectively, by R. M. Birn, et al., in "Separating respiratory-variation-related fluctuations from neuronal-activity-related fluctuations in fMRI," *NeuroImage*, 2006; 31:1536-1548, and by C. Chang, et al., in "Influence of heart rate on the BOLD signal: the cardiac response function," *NeuroImage*, 2009; 44:857-869. Effectively, RVT and CRT are differences between adjacent peaks and valleys in the respiratory volume and cardiac pulsation signals, respectively, normalized by the time elapsed between these peaks and valleys.

When the BOLD response to RVT and CRV is estimated while accounting for $PETCO_2$, the results differ from when the three are not fitted concurrently to the BOLD signal. Thus, the data-analysis approach described above considers the BOLD signal that has had the RVT or CRV contributions removed.

CVR Estimation Using Resting-State $PETCO_2$—rs-qCVR Method.

The methods described above with respect to FIGS. 1-3 and FIG. 5 were implemented in this study, as also illustrated in the proposed methodology outlined in FIG. 8. First, the $PETCO_2$ response function ($HRF_{CO2}$) was estimated from the resting-state BOLD signal, as per Eqn. (5). The onset time in BOLD response to $PETCO_2$ was also estimated. Specifically, the algorithm involves the following steps, which were described in more detail above.

First, the first 20 frames (~6.5 s) were discarded from the BOLD signal, and the rs-fMRI BOLD signal was bandpass filtered to between 0.005 and 0.4 Hz. The $PETCO_2$ trace was orthogonalized against CRV and RVT, such that all three signals were orthogonal to each other, and the signals were then downsampled to match the rs-fMRI data. The voxel-wise HRF for the residual (i.e., orthogonalized) CRV and RVT signals was estimated based on a multivariate deconvolution model. At each voxel, the orthogonalized CRV and RVT signals were convolved with their respective HRFs, and the results regressed from the preprocessed rs-fMRI data. The relationship between the resting BOLD signal and the $PETCO_2$ fluctuations was then estimated using the cross-correlation and the parametric deconvolution methods described above.

CVR Estimation Using rs-fMRI Signal Amplitude: Non-Quantitative rs-CVR Method.

Previous evidence has suggested that the rs-fMRI amplitude may in itself provide qualitative cerebrovascular reactivity estimates. Thus, two variants of the rs-fMRI amplitude were included in the comparison with the qCVR estimates.

In the first, the resting-state fluctuation amplitude ("RSFA") was used, which was computed as the temporal standard deviation of the preprocessed and band-pass filtered BOLD time course divided by the temporal mean, as described by S. S. Kannurpatti and B. B. Biswal in "Detection and scaling of task-induced fMRI-BOLD response using resting state fluctuations," *NeuroImage*, 2008; 40:1567-1574.

In the second, the amplitude of low-frequency fluctuations ("ALFF") was used, which was computed as the average square root of the frequency spectrum of the pre-processed and band-pass filtered BOLD time course, as described by Y. F. Zang, et al., in "Altered baseline brain activity in children with ADHD revealed by resting-state functional MRI," *Brain and Development*, 2007; 29:83-91.

CVR Estimation based on CO2 Challenge ("Gold Standard" qCVR).

To compute quantitative CVR for the "gold standard" comparison, the BOLD signal was computed by averaging consecutive tag and control images from the second echo of the pCASL data. First, the $CO_2$-response delay in BOLD time course was taken into account at each voxel. This delay was estimated from the phase difference between the BOLD or CBF time courses and that of $PETCO_2$, enabling the alignment of the fMRI and $PETCO_2$ time series for maximal correlation. For this alignment, both $PETCO_2$ and fMRI data were upsampled to a common higher frequency, such that delays that are shorter than TR could be measured.

Following the alignment, the PETCO$_2$ was interpolated to the pCASL TR and detrended at half the total duration of the respiratory paradigm. Outlier removal was performed based on Cook's distance from the initial linear model fit and the points with the Cook's distance greater than 4/N is discarded, where N is the number of time points. Subsequently, a linear model was fitted to the BOLD (dependent variable) and PETCO$_2$ (independent variable) values and CVR was defined as the slope of the linear model. The spatially specific CVR was thresholded at zero to minimize biases introduced by noise. Additionally, data associated with spiking in PETCO$_2$ time course was excluded.

The regional mean and standard deviation of the CVR estimates were computed across each motor ROI. Specifically, in order to generate representative regional CVR values unbiased by outliers, outlier voxels were first removed from each ROI using a non-parametric algorithm based on the Tukey's box-plot method. This method suited the present application as it does not assume a normal distribution for the voxel-wise CVR values.

Validation and Reproducibility Analysis.

The rsCVR maps were compared with the "gold-standard" CVR maps quantitatively. That is, 32 anatomical regions of interest (ROI) maps were generated and transformed into the functional space. Specifically, the parcellations were generated using probability-driven segmentation on the high-resolution anatomical scan acquired in the same session. The procedure included brain extraction, transformation into the MNI152 standard space, intensity normalization, tessellation of the gray matter white matter boundary, automated topology correction, and surface deformation following intensity gradients to optimally place the gray/white and gray/CSF borders at the location where the greatest shift in intensity defines the transition to the other tissue class.

"Gold-standard" CVR maps were also transformed into the functional space using the same program. By plotting CVR regional averages of the standard versus resting state CVR estimates, the feasibility of the methods could be assessed. As the CVR values were mapped on a per-ROI basis, variability in BOLD fMRI signal sensitivity and potential artifacts in different brain regions had to be accounted for. Thus, in this validation process, ROIs that contained less than 50% of non-zero data were excluded. Furthermore, a voxel outlier removal step then removed all voxels that contained values that were more than 1.96 standard deviations away from its ROI average. Subsequently, it was determined, using linear regression, whether a strong concordance existed between rs-qCVR and standard qCVR measures. By comparing the significance of the linear fit, as well as other statistical parameters, the quantitative-CVR methods of the present disclosure could also be compared against the qualitative methods (RSFA and ALFF).

Statistical significance of the regression was evaluated based on Student's t-test. In addition, the test-retest reproducibility of HRF$_{CO2}$ estimates were assessed by comparing HRF parameters, such as maximum amplitude and time-to-peak. Furthermore, the viability of estimating HRF$_{CO2}$ using conventional rs-fMRI acquisitions was assessed by comparing the estimates with those based on accelerated rs-fMRI acquisitions using the cosine-similarity index.

Results

Figure 9A:
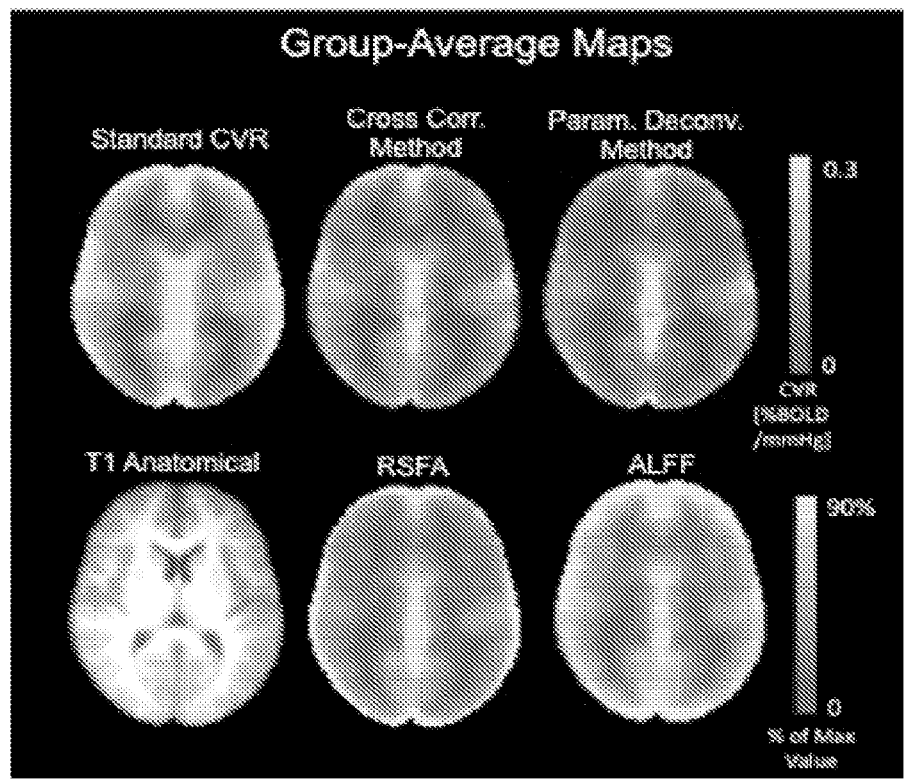
FIGS. 9A-9B depict CVR maps obtained using various approaches.
Figure 9B:
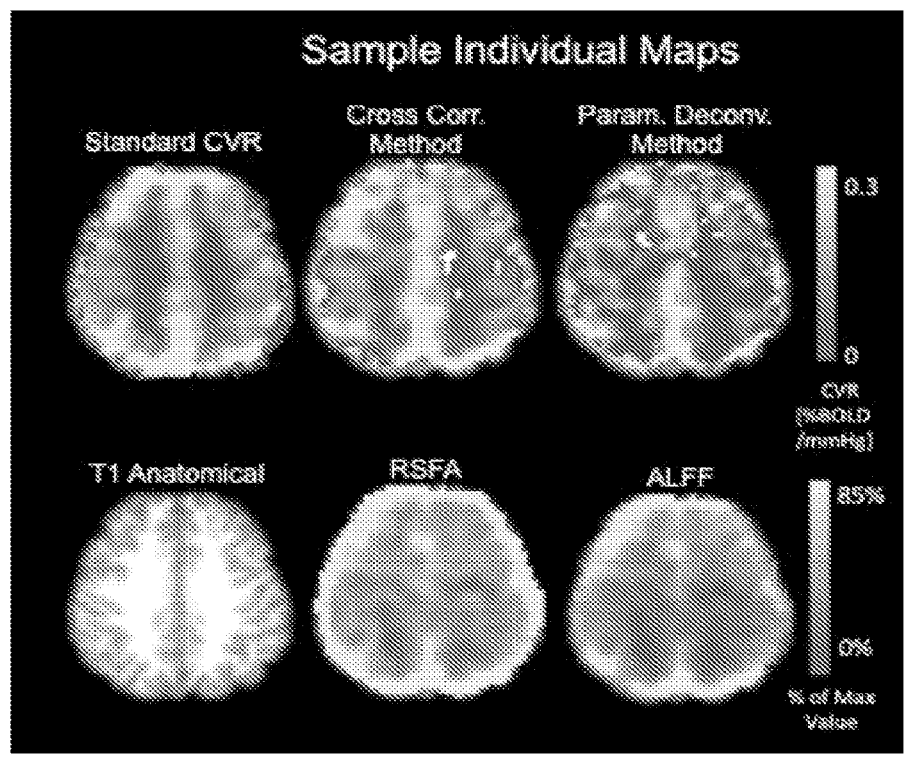

All 16 subjects were able to complete this study. For each subject, the standard CVR estimates were generated from CO$_2$ manipulations, as well as rs-fMRI-based CVR estimates, both quantitative (based on cross-correlation and parametric-deconvolution rs-qCVR methods) and qualitative (based on RSFA and ALFF metrics). The group averages of these maps are shown in FIG. 9A, while the maps of a representative subject are shown in FIG. 9B. All methods generated CVR maps with qualitative similarity to the standard CVR maps, in that grey matter regions exhibited higher CVR.

Figure 10:
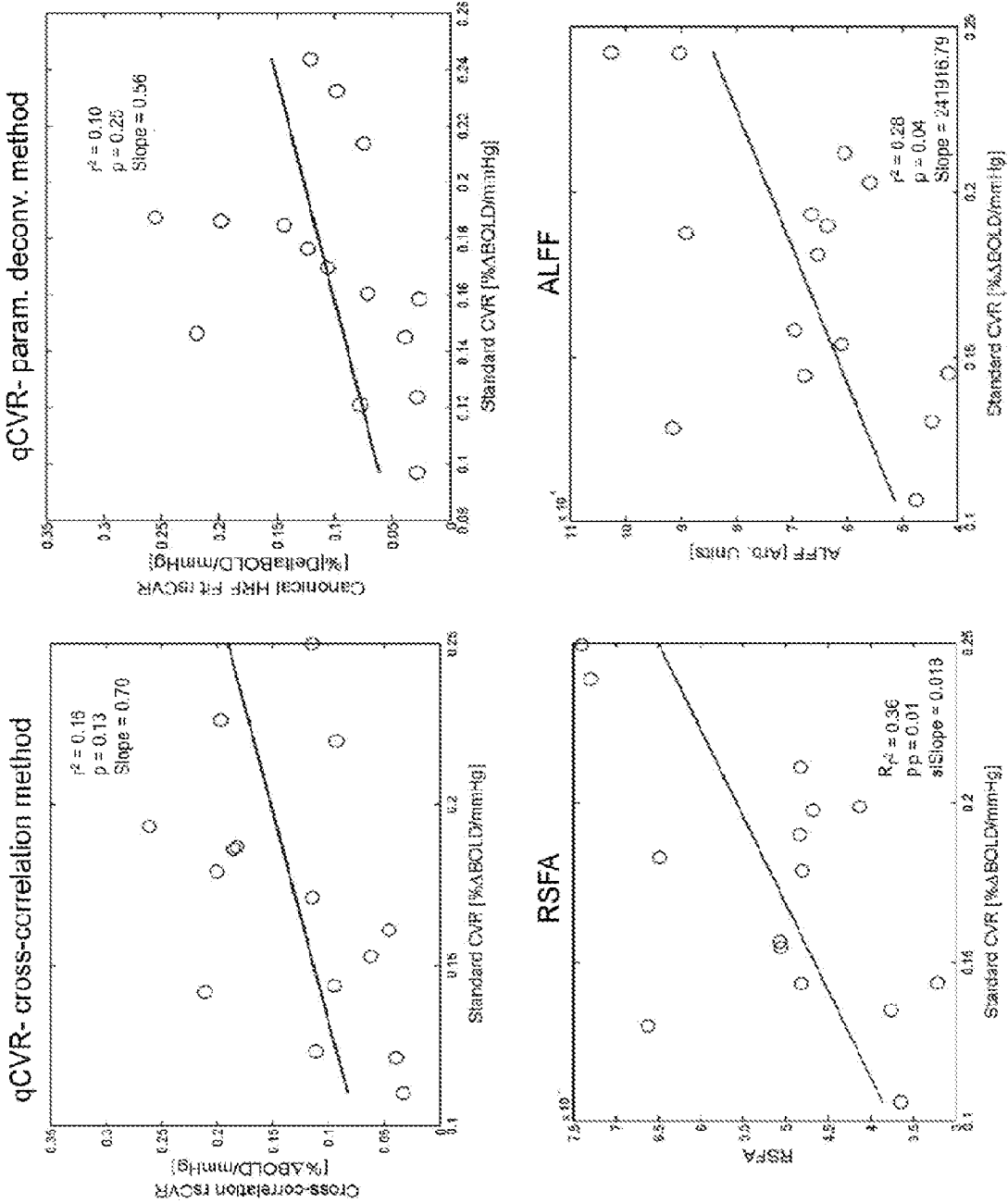
FIG. 10 shows the correspondence between rs-fMRI and "gold-standard" CVR estimates, based on global grey-matter averages. Each symbol represents the grey-matter average from one of 16 subjects. All methods examined achieved significant agreement with the standard.

In FIG. 10, initial quantitative comparisons of all methods to the standard CVR method are shown, through a group-wise examination of CVR values taken across all grey matter voxels. At this global level, all methods demonstrated significant cross-sectional agreement with the standard CVR method, as demonstrated through the p-values. However, this plot does not convey CVR estimation accuracy in terms of its spatial variations.

Figure 11:
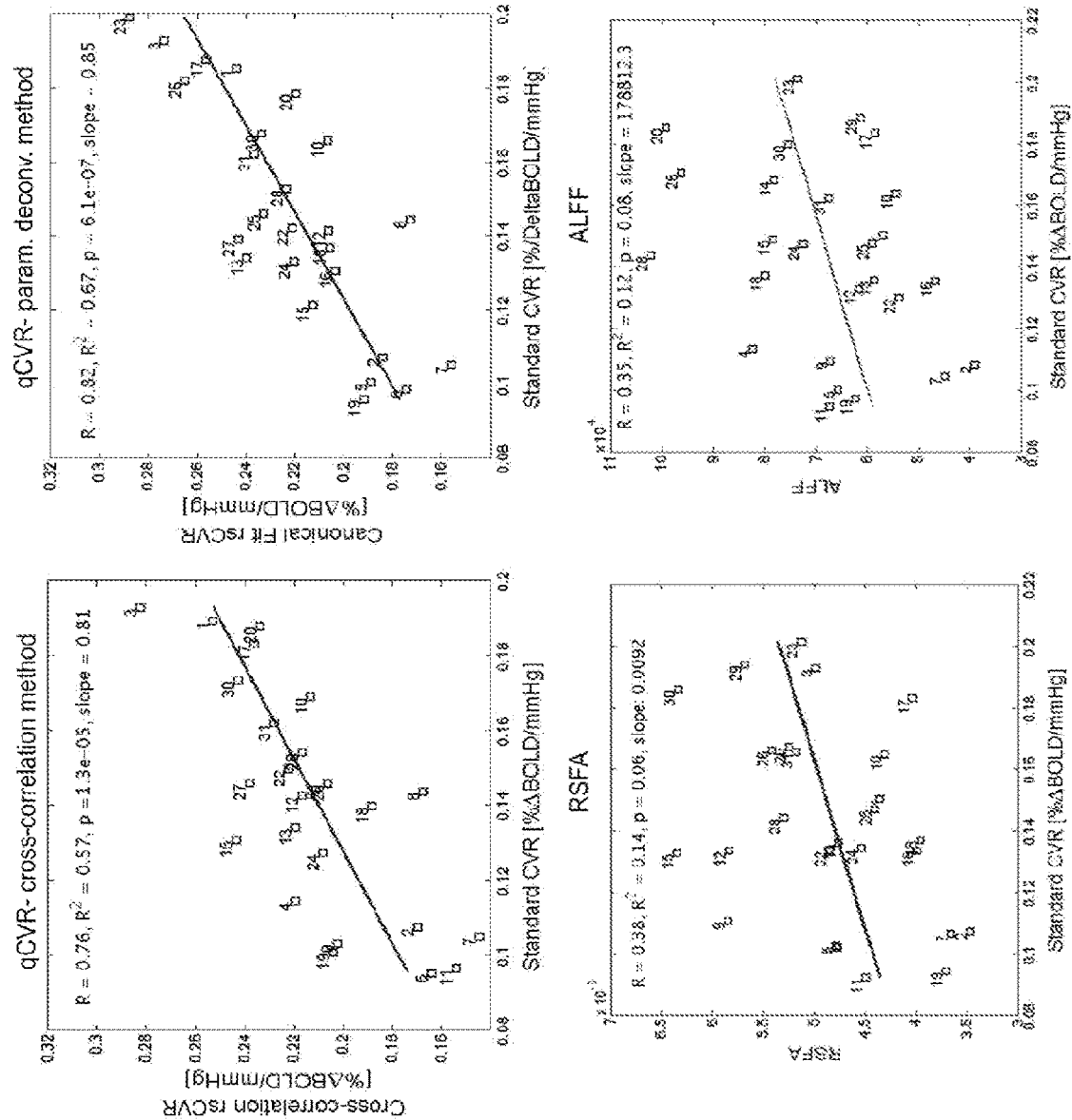
FIG. 11 shows the correspondence between rs-fMRI and "gold-standard" CVR estimates, based on within-subject agreement in different brain regions. Each symbol represents an ROI average CVR, with the number conveying the ROI definition.

In FIG. 11, the degree of within-subject agreement between the rs-fMRI-based and standard CVR methods is demonstrated for a representative subject. In this case, the distinction amongst the different methods begins to surface. With the quantitative CVR estimates produced by the parametric-deconvolution demonstrating the highest degree of agreement with CVR from the standard approach. In this cross-spatial examination, some common trends in terms of problematic regions for rs-fMRI-based CVR estimation (for all methods) were observed, predominantly the frontal pole, temporal pole, cuneus, inferior temporal regions. These regions typically contained poor signal-to-noise ratios, resulting in their exclusion from the within-subject fits. Moreover, upon closer examination, 3 data sets were associated with significant and repetitive motion that affected the PETCO$_2$ data. They were therefore excluded from the analyses, yielding a total of 13 subjects for the remainder of the analyses.

Figure 12A:
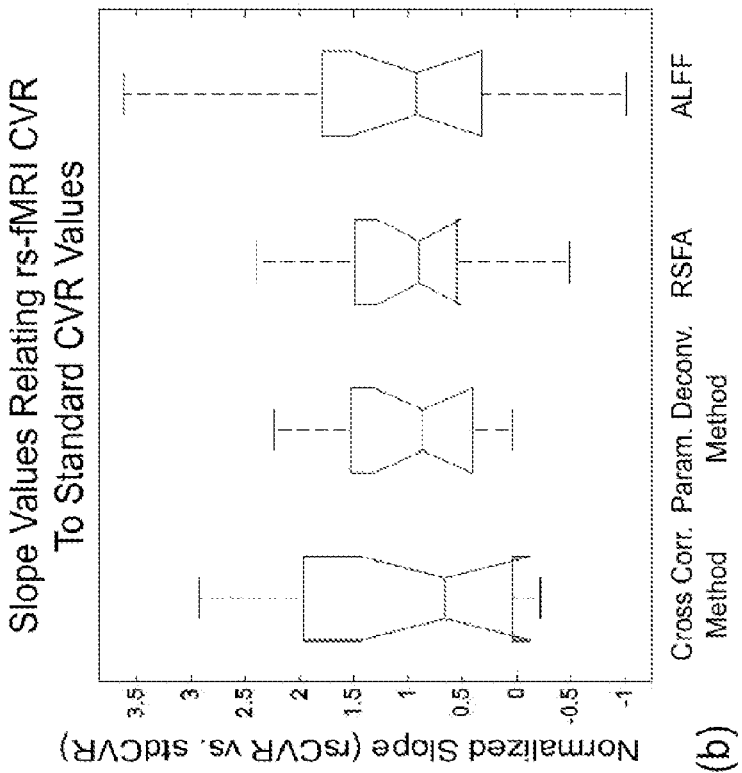
FIGS. 12A-12B show a summary comparison of different rs-fMRI CVR methods.
Figure 12B:
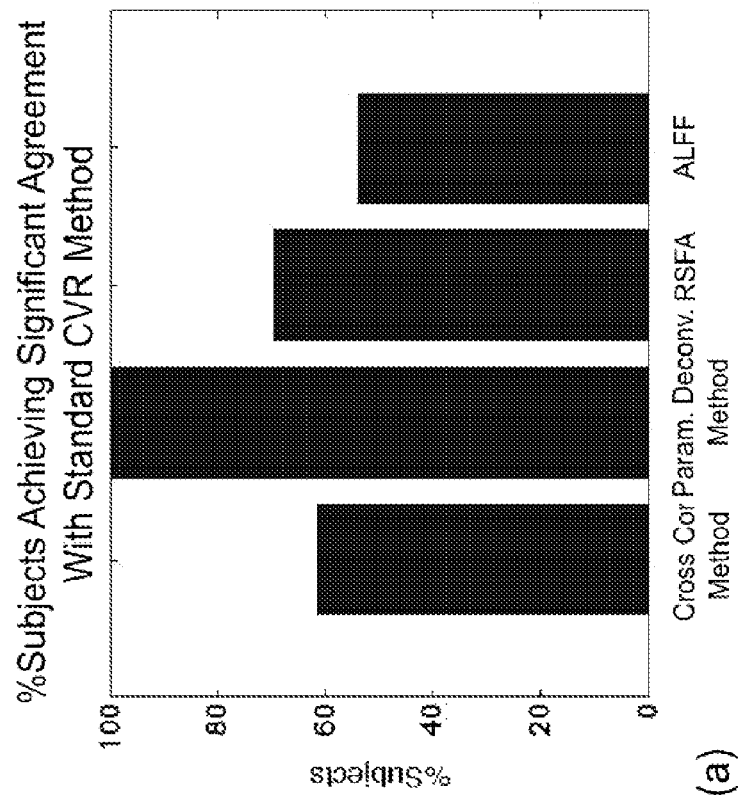

As summarized in FIG. 12A, the parametric-deconvolution rs-qCVR method produced the best agreement with the standard CVR approach, with the most number of subjects demonstrating significant or quasi-significant within-subject spatial associations between the rs-fMRI and standard CVR values. The rs-fMRI-based CVR values are typically related to standard quantitative CVR values through a scaling factor (labeled "slope"). This slope was found to be subject-dependent for all rs-fMRI-based methods. However, as shown in FIG. 12B, the slope associated with the parametric-deconvolution rs-qCVR method appeared to be the least variable with subject, followed by the slope of the RSFA method.

Figure 13A:
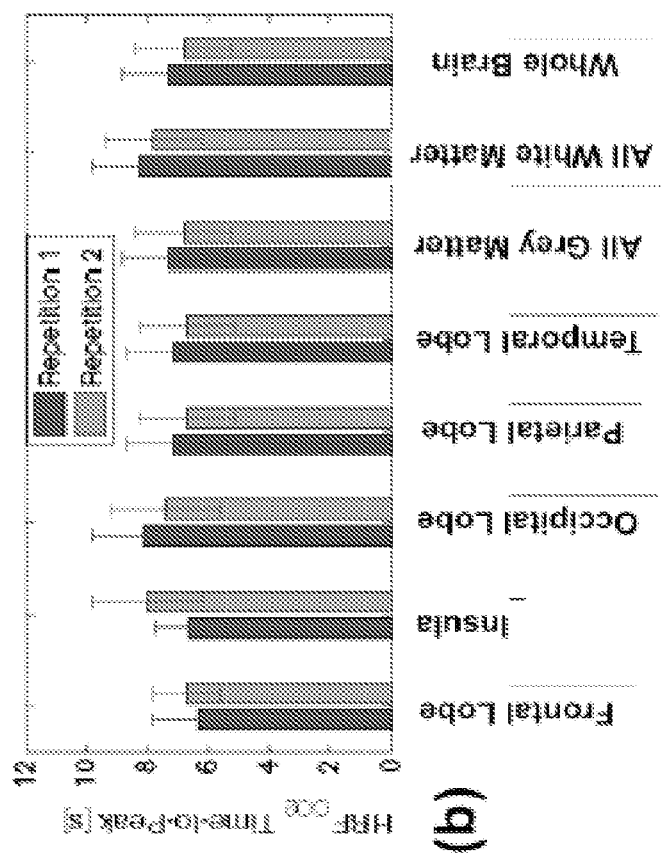
FIGS. 13A-13B illustrate the reproducibility of $HRF_{CO2}$ estimation.
Figure 13B:
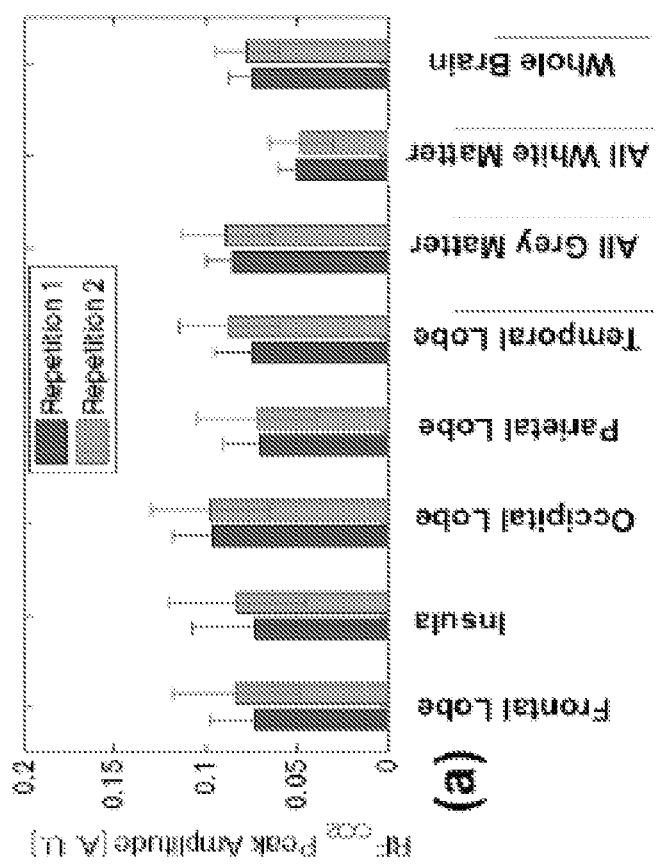
Figures 14A, 14B, 14C:
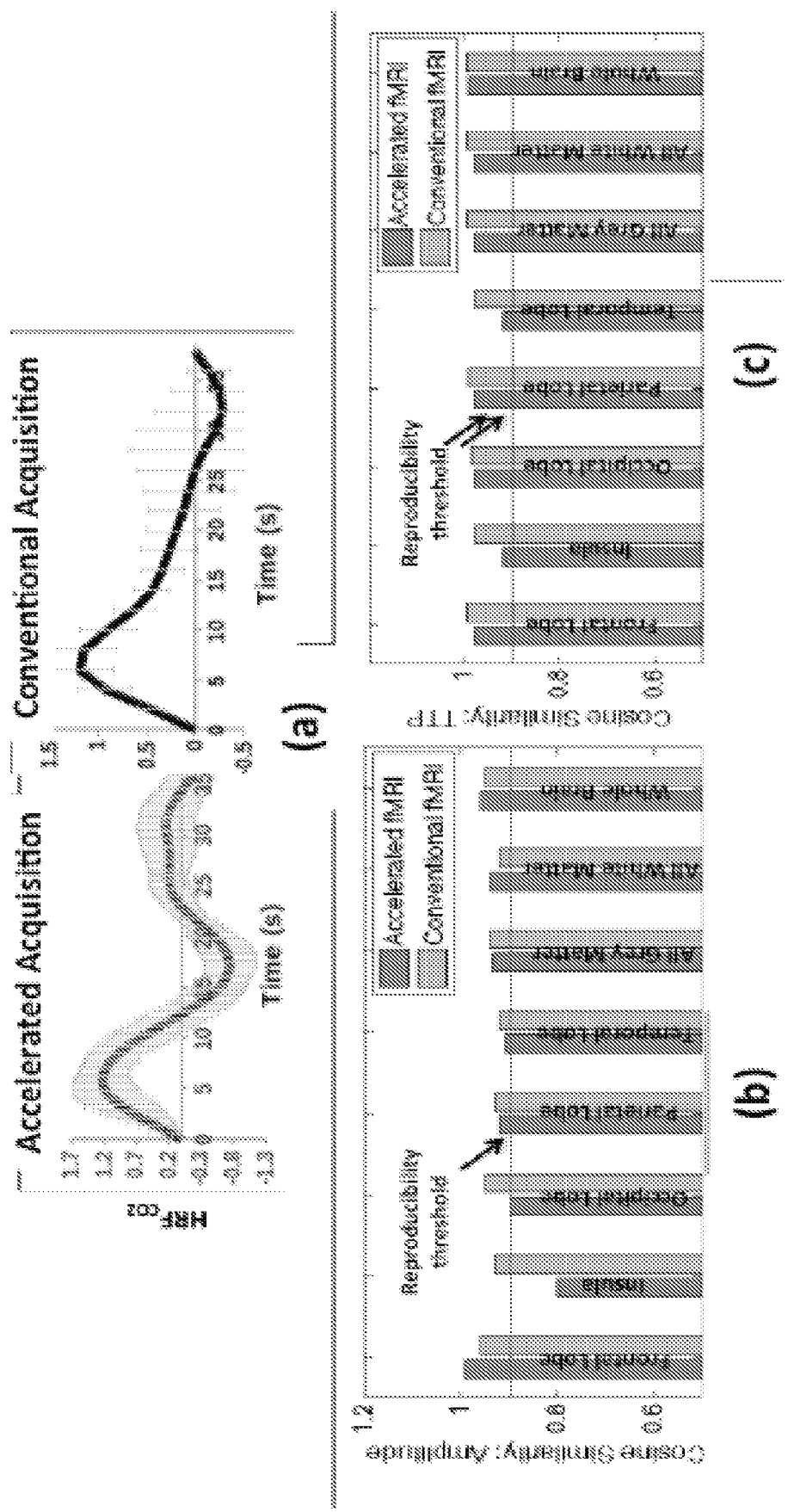
FIGS. 14A-14C illustrate the potential for estimating CVR using conventional rs-fMRI acquisitions.

Based on the reproducibility sub-study (FIGS. 13A-13B), HRF$_{CO2}$ estimates from repeat rs-fMRI scans in 5 healthy adults demonstrated highly similar outcomes, as quantified in terms of amplitude and time-to-peak, in multiple brain regions as well as across the whole brain. Furthermore, as shown in FIGS. 14A-14C, high between-scan cosine-similarity measures suggest that HRF$_{CO2}$ estimates (from 8 healthy subjects) were also comparable between accelerated and conventional (non-accelerated) fMRI acquisitions in the majority of brain regions.

DISCUSSION

The main findings of this example study were as follows. First, it is feasible to estimate quantitative CVR from rs-fMRI data with the aid of passive end-tidal CO$_2$, respiratory-volume, and cardiac pulsation recording. Second, compared to alternative and existing rs-fMRI-based methods, the parametric-deconvolution rs-qCVR method achieved of the present disclosure achieved substantially better agreement with the standard $CO_2$-challenge based CVR method. Third, the rs-fMRI-based method of the present disclosure is deemed reproducible. Although accelerated rs-fMRI acquisitions were implemented in this example study, it is contemplated that the analysis methodology of the present disclosure is feasible on non-accelerated rs-fMRI data sets.

The rs-fMRI-based qCVR method of the present disclosure offers a number of advantages. As one example, it circumvents measurement inconsistencies due to subject participation and differences in experimental protocol. As another example, instead of relying on a few hypercapnic or breathing task episodes, all spontaneous changes in $PETCO_2$ are considered in the qCVR measurement, resulting in potentially greater measurement reliability. Still another example advantage is that a resting-state method is completely non-invasive, and safe even for those with severe vascular risk factors. Additionally, the method of the present disclosure is much less demanding in terms of instrumentation and ease of implementation. As the need for subject cooperation is minimized, it is contemplated that the method of the present disclosure will have immediate impact for studying various clinical populations, even during general anesthesia, as occurs during neurosurgery.

The present disclosure has been described in terms of one or more preferred embodiments, and it should be appreciated that many equivalents, alternatives, variations, and modifications, aside from those expressly stated, are possible and within the scope of the invention.

The invention claimed is:

1. A method for estimating a quantitative cerebrovascular reactivity from resting-state functional magnetic resonance imaging data, the method comprising:
   (a) providing resting-state functional magnetic resonance imaging (rs-fMRI) data acquired from a subject with a magnetic resonance imaging (MRI) system, the rs-fMRI data comprising blood-oxygen level dependent (BOLD) signals;
   (b) providing physiological data acquired from the subject while the rs-fMRI data were acquired, the physiological data comprising cardiac-rate variability (CRV) signals, respiratory-volume variability (RVT) signals, and passive end-tidal carbon dioxide (PETCO2) signals;
   (c) processing the BOLD signals to remove BOLD signal variations attributable to the CRV and RVT signals by orthogonalizing the CRV signals, RVT signals, and PETCO2 signals to a common orthogonal basis and regressing out the orthogonalized CRV and RVT signals from the BOLD signals;
   (d) estimating the quantitative cerebrovascular reactivity (qCVR) from the processed BOLD signals by further processing the BOLD signals to remove BOLD signal variations attributable to the PETCO2 signals, wherein further processing the BOLD signals includes estimating the qCVR based on a cross-correlation between the PETCO2 signals and the processed BOLD signals; and
   (e) generating and displaying to a user, a qCVR map based on the qCVR estimated from the processed BOLD signals, wherein the qCVR maps depict a spatial distribution of qCVR values in the subject relative to anatomy of the subject.

2. The method as recited in claim 1, wherein regressing out the orthogonalized CRV and RVT signals from the BOLD signals includes:
   estimating a voxelwise hemodynamic response function (HRF) for the CRV signals and for the RVT signals;
   generating convolved CRV signals by convolving the voxelwise HRF for the CRV signals with the orthogonalized CRV signals;
   generating convolved RVT signals by convolving the voxelwise HRF for the RVT signals with the orthogonalized RVT signals; and
   regressing out the convolved CRV and convolved RVT signals from the BOLD signals.

3. The method as recited in claim 2, wherein estimating the voxelwise HRF for the CRV signals and the voxelwise HRF for the RVT signals includes estimating each HRF using a multivariate deconvolution model.

4. The method as recited in claim 1, wherein step (c) includes downsampling the CRV signals, RVT signals, and PETCO2 signals to a sampling rate of the BOLD signals.

5. The method as recited in claim 1, wherein estimating the qCVR includes:
   determining a time lag that maximizes the cross-correlation between the PETCO2 signals and the processed BOLD signals;
   truncating the PETCO2 signals and the processed BOLD signals based on the time lag;
   performing a regression of the truncated PETCO2 signals and the truncated BOLD signals; and
   selecting the qCVR as a slope of the regression.

6. A method for estimating a quantitative cerebrovascular reactivity from resting-state functional magnetic resonance imaging data, the method comprising:
   (a) providing resting-state functional magnetic resonance imaging (rs-fMRI) data acquired from a subject with a magnetic resonance imaging (MRI) system, the rs-fMRI data comprising blood-oxygen level dependent (BOLD) signals;
   (b) providing physiological data acquired from the subject while the rs-fMRI data were acquired, the physiological data comprising cardiac-rate variability (CRV) signals, respiratory-volume variability (RVT) signals, and passive end-tidal carbon dioxide (PETCO2) signals;
   (c) processing the BOLD signals to remove BOLD signal variations attributable to the CRV and RVT signals by orthogonalizing the CRV signals, RVT signals, and PETCO2 signals to a common orthogonal basis and regressing out the orthogonalized CRV and RVT signals from the BOLD signals;
   (d) estimating the quantitative cerebrovascular reactivity (qCVR) from the processed BOLD signals by further processing the BOLD signals to remove BOLD signal variations attributable to the PETCO2 signals, wherein further processing the BOLD signals includes estimating the qCVR using a parametric deconvolution based on the PETCO2 signals and the processed BOLD signals; and
   (e) generating and displaying to a user, a qCVR map based on the qCVR from the processed BOLD signals, wherein the qCVR maps depict a spatial distribution of qCVR values in the subject relative to anatomy of the subject.

7. The method as recited in claim 6, wherein estimating the qCVR includes:
   determining a CO2 hemodynamic response function (HRFCO2) from the PETCO2 signals;
   performing a regression of the HRFCO2 and the processed BOLD signals; and
   selecting the qCVR as a slope of the regression.

8. The method as recited in claim 7, wherein determining the HRFCO2 includes:

determining a canonical hemodynamic response function (HRF);

computing a temporal derivative of the canonical HRF;

computing a dispersion derivative of the canonical HRF; and computing the HRFCO2 based on a basis function set defined by the canonical HRF, the temporal derivative of the canonical HRF, and the dispersion derivative of the canonical HRF.

9. The method as recited in claim 8, wherein computing the HRFCO2 includes determining relative contributions of each basis function in the basis function set based on a least-squares minimization of a difference between the processed BOLD signals and a convolution between the HRFCO2 and the PETCO2 signals.

10. The method as recited in claim 8, wherein the temporal derivative of the canonical HRF is computed as a Taylor expansion of the canonical HRF in time, and the dispersion derivative of the canonical HRF is computed as a Taylor expansion of the canonical HRF width.

11. The method as recited in claim 8, wherein the canonical HRF is determined based on an initialized HRF characterized by a parameter set.

12. The method as recited in claim 6, wherein regressing out the orthogonalized CRV and RVT signals from the BOLD signals includes:

estimating a voxelwise hemodynamic response function (HRF) for the CRV signals and for the RVT signals;

generating convolved CRY signals by convolving the voxelwise HRF for the CRV signals with the orthogonalized CRV signals;

generating convolved RVT signals by convolving the voxelwise HRF for the RVT signals with the orthogonalized RVT signals; and regressing out the convolved CRV and convolved RVT signals from the BOLD signals.

13. The method as recited in claim 12, wherein estimating the voxelwise HRF for the CRY signals and the voxelwise HRF for the RVT signals includes estimating each HRF using a multivariate deconvolution model.

14. The method as recited in claim 6, wherein step (c) includes downsampling the CRV signals, RVT signals, and PETCO2 signals to a sampling rate of the BOLD signals.

* * * * *

UNITED STATES PATENT AND TRADEMARK OFFICE
CERTIFICATE OF CORRECTION

PATENT NO. : 10,898,143 B2
APPLICATION NO. : 15/348017
DATED : January 26, 2021
INVENTOR(S) : Jing Jean Chen, Ali M. Golestani and Luxi Wei Page 1 of 1

It is certified that error appears in the above-identified patent and that said Letters Patent is hereby corrected as shown below:

In the Claims

Claim 12, Column 18, Line 6: "CRY" should be "CRV"
Claim 13, Column 18, Line 16: "CRY" should be "CRV"

Signed and Sealed this
Twenty-sixth Day of April, 2022

Katherine Kelly Vidal
*Director of the United States Patent and Trademark Office*